United States Patent [19]

Palmer et al.

[11] Patent Number: 5,061,726
[45] Date of Patent: Oct. 29, 1991

[54] ALKYNYLPHENYL-SUBSTITUTED 1,3-OXATHIONE COMPOUNDS WITH PESTICIDAL ACTIVITY

[75] Inventors: Christopher J. Palmer, Ipswich, England; John E. Casida, Berkeley, Calif.; John P. Larkin, Bedfordhire, England

[73] Assignee: The Regents of the University of California, Oakland, Calif.

[21] Appl. No.: 514,011

[22] Filed: Apr. 26, 1990

Related U.S. Application Data

[63] Continuation-in-part of Ser. No. 330,404, Mar. 30, 1989, abandoned.

[51] Int. Cl.$^5$ .................. A61K 31/385; C07D 327/06
[52] U.S. Cl. ........................................ 514/433; 549/4; 549/14; 546/14; 546/268; 514/63; 514/336
[58] Field of Search ............... 549/4, 14; 514/63, 336, 514/433; 546/14, 268

[56] References Cited

U.S. PATENT DOCUMENTS 4,220,561  8/1980  Winter et al. .................. 252/22

FOREIGN PATENT DOCUMENTS 7404474  11/1974  Netherlands.

Primary Examiner—Richard L. Raymond
Assistant Examiner—Mark W. Russell
Attorney, Agent, or Firm—Nixon & Vanderhye

[57] ABSTRACT

Pesticidally-active alkynylphenyl-substituted 1,3-oxathianes and related substituted compounds of the formula:

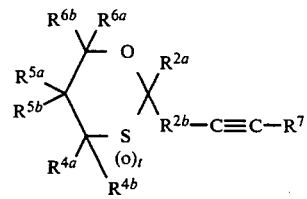

and their use in controlling pests such as arthropods and helminths are described.

30 Claims, No Drawings

ALKYNYLPHENYL-SUBSTITUTED 1,3-OXATHIONE COMPOUNDS WITH PESTICIDAL ACTIVITY

This invention was made with United States Government support under Grant No. PO1 ES 00049 from the National Institutes of Health to The University of California. The United States Government has certain rights in this invention.

This application is a Continuation in Part of U.S. Ser. No. 07/330404 filed Mar. 30 1989.

The present invention is concerned with a method of controlling pests such as arthropods, e.g. insects and acarine pests, and helminths, e.g. nematodes, by contacting the pests with novel pesticides. The invention is also concerned with the novel pesticides used for controlling the pests and processes for making such pesticides.

Current classes of pesticides effectively control some but not all pest species. It is also desirable to have new classes of pesticides since pests tend to develop resistance to any one pesticide, or sometimes to any one class of pesticide, after they have been selected with or exposed to such pesticides over a period of time.

Certain 2,5-dialkylsubstituted dithianes have been investigated as liquid crystal materials (see for example Mol. Cryst. Liq. Cryst. 131. 101) and more recently we have discovered that, inter alia. 2-substituted-5-tertiary butyldithianes have interesting pesticidal activity (European Patent Application No. 294229). The corresponding 2-substituted-5-tertiarybutyldioxanes have little pesticidal activity however. It has been discovered that a class of novel 2,5-disubstituted oxathianes has pesticidal activity. The extent of activity of the oxathianes is very dependent on the nature of the substituent at the 2-position and it has been found that having a group at the 2-position that contains an ethynyl fragment gives excellent activity. Accordingly, the present invention provides a compound of the formula (I):

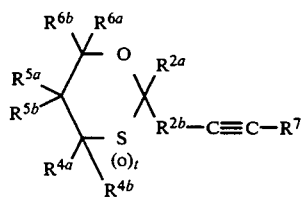

which contains between 10 and 27 carbon atoms, and wherein t is selected from 0. 1 and 2; $R^{2a}$ is hydrogen, methyl, or ethyl; $R^{2b}$ is a single bond, a $C_{5-7}$ cycloalkyl group or a group $(CH_2)_n(X)_m(CH_2)_{n'}$ optionally substituted by one to six halo atoms which are the same or different and/or by one or two alkyl groups optionally substituted by halo wherein n is 0, 1 or 2, X is oxygen, sulphur or CH=CH, m is 0 or 1 and n' is 0 to 4. the sum of n, m and n' between 0 and 6 or $R^{2b}$ is a para-substituted 6-membered aromatic ring additionally optionally substituted by one to four halo atoms and/or by one or two cyano groups and/or by one or two $C_{1-4}$ haloalkyl, haloalkoxy or haloalkylthio groups, and $R^7$ is hydrogen, halo or a $C_{1-5}$ hydrocarbyl group, optionally substituted by a hydroxy, $C_{1-4}$ alkoxy or $C_{1-7}$ acyloxy group and/or by one to five halo atoms which are the same or different and/or by a group $—(O)_vS(O)_r(O)_w R^8$ wherein $R^8$ is a $C_{1-4}$ aliphatic group optionally substituted by halo, v is 0 or 1, r is 0, 1 or 2 and w is 0 or 1, the sum of v, r and w being between 0 and 3 or $R^7$ is a group $SiR^9R^{10}R^{11}$ wherein $R^9$, $R^{10}$ and $R^{11}$ are the same or different and are each $C_{1-14}$ aliphatic groups provided that $R^9$, $R^{10}$ and $R^{11}$ do not contain more than 10 carbon atoms in total; $R^{4a}$, $R^{4b}$, $R^{6a}$ and $R^{6b}$ are the same or different and are chosen from hydrogen, methyl, trifluoromethyl or cyano; $R^{5a}$ is a group

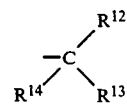

wherein $R^{12}$ is methyl, ethyl, chloro, bromo, methoxy, cyano, nitro, methoxymethyl, $C_{1-4}$ carbalkoxy or trifluoromethyl, $R^{13}$ is chloro, methyl or trifluoromethyl or

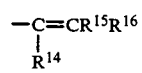

is a

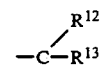

group wherein $R^{15}$ and $R^{16}$ are both hydrogen, methyl, trifluoromethyl, fluoro, chloro or bromo or $R^{15}$ is hydrogen and $R^{16}$ is fluoro, chloro or bromo, or

is a three or four membered ring, wherein $R^{12}$ is oxygen or a group $CR^{17}R^{18}$ wherein the groups $R^{17}$ and $R^{18}$ are the same or different and each is hydrogen, fluoro, chloro or bromo or methyl or ethyl optionally substituted by 1 to 5 fluoro atoms, when

is a three membered ring $R^{13}$ is a group $CR^{17a}R^{18a}$ wherein $R^{17a}$, $R^{18a}$ are the same or different and each is hydrogen, fluoro, chloro or bromo or methyl or ethyl optionally substituted by 1 to 5 fluoro atoms, or when

is a four membered ring $R^{13}$ is a group $CR^{17a}R^{18a}CR^{19}R^{20}$ wherein $R^{17a}$, $R^{18a}$ are as hereinbefore defined, and $R^{19}$, and $R^{20}$ are the same or different and each is hydrogen, fluoro, chloro or bromo or methyl or ethyl optionally substituted by 1 to 5 fluoro atoms, and $R^{14}$ is hydrogen, methyl, trifluoromethyl, iodo, fluoro, chloro or bromo; and $R^{5b}$ is hydrogen, methyl, hydroxy, methoxy, acetoxy, halo or trifluoromethyl.

By the term "hydrocarbyl" group is meant an alkyl, alkenyl or alkynyl group (including a cyclic alkyl or alkenyl group optionally substituted by alkyl, alkenyl or alkynyl; and alkyl or alkenyl substituted by cyclic alkyl and alkenyl).

By the term "6-membered aromatic ring" is meant phenyl and a heteroaromatic ring of which pyridyl is an example.

By the term "halo" is meant fluoro, chloro, bromo or iodo.

When $R^{2b}$ contains a sulphur atom, this may be present in an oxidised form.

$R^{2b}$ suitably contains between 0 and 8 carbon atoms. $R^{2b}$ is suitably a single bond, a $C_{3-6}$ alkyl or alkenyl group or a phenyl or cyclohexyl group, each of which may be optionally substituted by halo or $C_{1-3}$ haloalkyl. When a silyl group is present this is normally adjacent to an ethynyl, ethenyl or ethyl group and suitably is adjacent to an ethynyl group. Preferably there is only one silyl group present.

Preferably $R^7$ is hydrogen, bromo, chloro, iodo or a $C_{1-5}$ aliphatic group optionally substituted by $C_{1-4}$ alkoxy, $C_{1-7}$ acyloxy, halo or hydroxy; or $R^7$ is $SiR^9 R^{10} R^{11}$ wherein $R^9$, $R^{10}$ and $R^{11}$ are as hereinbefore defined.

In one suitable embodiment $R^{2b}$ is a phenyl group, substituted at the 4-position by a group $C\equiv C-R^7$ wherein $R^7$ is as hereinbefore defined and optionally substituted by one or two additional substituents at the 3-and/or 5-positions each selected from halo, $C_{1-4}$ haloalkyl, $C_{1-4}$ haloalkoxy, $C_{1-4}$ haloalkylthio or cyano. The phenyl group is additionally optionally substituted at the 2- and/or 6-positions by fluoro or chloro.

In one preferred embodiment $R^{2b}$ is phenyl substituted at the 4-position by a group $C\equiv C-R^{21}$ where $R^{21}$ is hydrogen, methyl, or ethyl each optionally substituted by hydroxy, methoxy, ethoxy, acetoxy; or $R^{21}$ is a silyl group substituted by three $C_{1-4}$ alkyl groups. The phenyl group is additionally optionally substituted by fluoro or chloro.

In a second preferred embodiment is a single bond, a $C_{3-5}$ aliphatic chain optionally containing a double bond and/or an oxygen atom and/or a group $S(O)q$ wherein q is 0, 1 or 2, optionally substituted by halo, $C_{1-4}$ alkyl or $C_{1-4}$ haloalkyl. When $R^{2b}$ is a single bond, $R^7$ is preferably a tertiary alkyl group in which one of the alkyl groups may be replaced by methoxy.

Preferably $R^{2a}$ is hydrogen or methyl.

Preferably $R^{4a}$, $R^{4b}$, $R^{6a}$ and $R^{6b}$ are hydrogen.

Preferably $R^{5a}$ is tertiary butyl or isopropyl.

Suitably $R^{5b}$ is hydrogen or methyl. Preferably $R^5$ is hydrogen.

In a third preferred embodiment $R^{2b}$ is a 1,4-disubstituted cyclohexyl group.

Preferred compounds of the present invention include:
5(e)-t-butyl-2(e)-(4-ethynylphenyl)-1,3-oxathiane.
5(e)-t-butyl-2(e)-(4-ethynylphenyl)-1,3-oxathiane 3-oxide.
5(e)-t-butyl-2(e)-(4-ethynylphenyl)-1,3-oxathiane 3,3-dioxide.
5(e)-t-butyl-2(e)-(hex-5-ynyl)-1,3-oxathiane.
5(e)-t-butyl-2(e)-(hex-5-ynyl)-1,3-oxathiane 3,3-dioxide.
trans/cis-2-(hex-5-ynyl)-5-isopropyl-1,3-oxathiane.
2(e)-(hex-5-ynyl)-5(e)-isopropyl-1,3-oxathiane 3,3-dioxide.
trans/cis-2-(hex-5-ynyl)-5-isopropyl-1,3-oxathiane 3,3-dioxide.
trans/cis-2-(4-ethynylcyclohexyl)-5-isopropyl-1,3-oxathiane.
2(e)-(4-ethynylphenyl)-5(e)-isopropyl-1,3-oxathiane 3,3-dioxide.
2(e)-(4-ethynylphenyl)-5(e)-isopropyl-1,3-oxathiane 3-oxide.
2(a)-(4-ethynylphenyl)-5(e)-isopropyl-1,3-oxathiane 3-oxide.
2(e)-(4-ethynylphenyl)-5(e)-phenyl-1,3-oxathiane.
2(e)-(4-ethynylphenyl)-5(e)-phenyl-1,3-oxathiane 3,3-dioxide.
2(e)-(hex-5-ynyl)-5(e)-phenyl-1,3-oxathiane 3,3-dioxide.
5(e)-t-butyl-2(e)-(4-ethynyl-3-fluorophenyl)-1,3-oxathiane.
trans/cis-5-t-butyl-2-(4-ethynylcyclohexyl)-1,3-oxathiane.
5(e)-t-butyl-6(e)-methyl-2(e)-(4-trimethylsilylethynylphenyl)-1,3oxathiane.
5(e)-t-butyl-2(e)-(4-ethynylphenyl)-6-methyl-1,3-oxathiane.
5(e)-t-butyl-2(e)-(4-ethynylphenyl)-6(e)-methyl-1,3-oxathiane 3,3-dioxide.
5(e)-t-butyl-2(a)-(4-ethynylphenyl)-6(e)-methyl-1,3-oxathiane 3,3-dioxide.

The compounds of the formula (I) may exist in a number of stereoisomeric forms. The present invention encompasses both individual conformational and stereoisomers and mixtures thereof. The present invention also encompasses radiolabelled compounds of the formula (I), particularly those in which one carbon atom is $C^{14}$ or one or more hydrogen atoms are replaced by tritium.

A preferred group of compounds are defined by the formula:

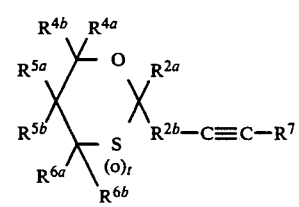

which contains between 10 and 27 carbon atoms, wherein t=0, and 2; $R^{2a}$ is hydrogen, methyl, or ethyl; $2^{2b}$ is a single bond, a $C_{5-7}$ cycloalkyl group or a group $(CH_2)_n(X)_m(CH_2)_{n}$, optionally substituted by one to six halo atoms, which are the same or different, and/or by one or two alkyl groups optionally substituted by halo, where n is 0, 1 or 2, X is oxygen, sulphur or $CH=CH$, m is 0 or 1 and n' is 0 to 4, the sum or n, m and n' is between 0 and 6. Alternatively, $R^{2b}$ is a para-substituted 6-membered aromatic ring additionally optionally substituted by one to four halo atoms and/or by one or two cyano groups and/or by one or two $C_{1-4}$ haloalkyl, haloalkoxy or haloalkylthio groups, $R^7$ is hydrogen, halo or a $C_{1-5}$ hydrocarbyl group, optionally substituted by a hydroxy, $C_{1-4}$ alkoxy or $C_{1-7}$ acyloxy group derived from carboxylic acid and/or by one to five halo atoms which are the same or different and/or by a group $-(O)_vS(O)_r(O)_wR^8$ where $R^8$ is a $C_{1-4}$ hydrocarbyl aliphatic group optionally substituted by halo, v is 0 or 1, r is 0, 1 or 2 and w is 0 or 1, provided the sum of v, r and w is between 0 and 3. Alternatively, $R^7$ is a group $SiR^9 R^{10} R^{11}$ where $R^9$, $R^{10}$, and $R^{11}$ are the same or different and are each $C_{1-4}$ aliphatic groups, provided that $R^9$, $R^{10}$ and $R^{11}$ do not contain more than 10 carbon atoms in total. $R^{4a}$, $R^{4b}$, $R^{6a}$ and $R^{6b}$ are the same or different and are chosen from hydrogen, methyl, trifluoromethyl or cyano. $R^{5b}$ is hydrogen, methyl, hydroxy, methoxy, acetoxy, halo or trifluoromethyl, and $R^{5a}$ is tert. butyl, cyclobutyl, 1-methyl-cyclopropyl or isopropyl.

Preferably, $R^{2b}$ is a single bond, a $C_{3-6}$ alkyl or alkenyl group, a phenyl or cyclohexyl group, each of which may be optionally substituted by halo or $C_{1-3}$ haloalkyl. Also, $R^{2b}$ may be a phenyl group, substituted at the 4-position by a group $C\equiv C-R^7$ and optionally substituted by one or two additional substituents at the 3- and/or 5-positions each selected from halo, $C_{1-4}$ haloalkyl, $C_{1-4}$ haloalkyl, $C_{1-4}$ haloalkoxy, $C_{1-4}$ haloalkylthio or cyano and where the phenyl group is optionally substituted at the 2-and/or 6-positions by fluoro or chloro. $R^{2b}$ may also be phenyl substituted at the 4-position by a group $C\equiv CR^{12}$ where $R^{12}$ is hydrogen, methyl, or ethyl each optionally substituted by hydroxy, methoxy, ethoxy, or acetoxy; or $R^{12}$ is a silyl group substituted by three $C_{1-4}$ alkyl groups, and wherein the phenyl group is additionally optionally substituted by fluoro or chloro.

Additionally, $R^{2b}$ is a single bond, a $C_{3-5}$ aliphatic chain optionally containing a double bond and/or an oxygen atom and/or a group $S(O)_q$ where q is 0, 1 or 2, optionally substituted by halo, $C_{1-4}$ alkyl or $C_{1-4}$ haloalkyl. Desirably $R^{2b}$ is a 1,4-disubstituted cyclohexyl group.

In this compound $R^7$ may be hydrogen, bromo, chloro, iodo or a $C_{1-5}$ aliphatic group derived from carboxylic acid optionally substituted by $C_{1-4}$ alkoxy, $C_{1-7}$ acyloxy, halo or hydroxy or $R^7$ is $SiR^9 R^{10} R^{11}$ where $R^9$, $R^{10}$ and $R^{11}$ are ad defined above.

$R^{5a}$ is preferably tert. butyl.

Pesticidal formulations containing a pesticidally effective amount of such compounds in admixture with one or more carriers or diluents and/or synergists and/or one or more pesticidally active ingredients, attractants, repellents, bacteriocides, fungicides and/or anthelmintics are also contemplated.

Use of the compounds for the control of arthropod and/or helminth infestations of plants and/or animals and/or stored products by administering an effective amount of these compounds is also contemplated.

The present invention also provides for the preparation of the compounds of the formula (I) by methods derived from those known in the art for the preparation of analogous compounds. Thus, the compounds may be prepared by (i) the reaction of a compound of the formula (II):

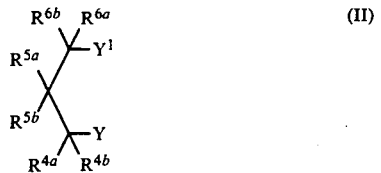

(II)

wherein Y is SH and $Y^1$ is OH with a suitable aldehyde or ketone of the formula

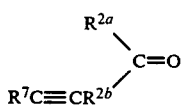

or a reactive derivative thereof, wherein $R^{21}$, $R^{2b}$, $R^{4a}$, $R^{4b}$, $R^{5a}$, $R^{5b}$, $R^{6a}$ and $R^{6b}$ are as hereinbefore defined and, if required, thereafter oxidizing the ring sulphur atom.

The reaction is suitably carried out in the presence of a catalyst or of a dehydrating agent in a non-polar solvent at a non-extreme temperature. Suitable catalysts include a dimethyl formamide/dimethyl sulphate catalyst and catalysts such as sulphonic acids or perfluorinated resins thereof or Lewis acids such as boron trifluoride etherate. Suitable solvents include hydrocarbons such as benzene, toluene or xylene or chlorinated hydrocarbons such as dichloromethane. The reaction is normally performed between 0° and 200° and conveniently between 20° and 120°.

Suitable reactive derivatives of aldehydes and ketones include acetals and ketals.

The compounds of the formula (II) may be prepared from the corresponding diols wherein Y and $Y^1$ are hydroxy via a sulphonate or halo derivative (i.e., a compound of the formula (II) wherein Y is a group $OSO_2R^{22}$ where $R^{22}$ is $C_{1-4}$ alkyl or para-tolyl, or Y is halo and $Y^1$ is a protected hydroxy group, for example a benzyloxy or acetoxy group). or similar leaving group such as bromo or chloro, as described in the Examples herein.

The aldehydes and ketones reacted with the hydroxythiols of the formula (II) are either known in the literature or are prepared by literature methods.

(ii) When it is required to prepare a compound of the formula (I) wherein $R^{2b}$ is a phenyl group, this is carried out by the reaction of the corresponding optionally substituted para-iodophenyl compound with a compound $HC\equiv CR^7$ wherein $R^7$ is as hereinbefore defined other than hydrogen. This reaction is carried out in the presence of a suitable palladium catalyst well known to those skilled in the art for this type of reaction, for example bistriphenylphosphine palladium dichloride, and a catalytic amount of a cuprous halide, such as cuprous iodide. The reaction will normally be carried out in the presence of basic solvent such as diethylamine or triethylamine at a non-extreme temperature, for example between $-50°$ and $100°$ and conveniently at room temperature. The starting material, i.e. the iodophenyl oxathiane may be prepared as described above.

It is often convenient to prepare compounds of the formula (I) by interconversion from other compounds of the formula (I), for example:

(a) when it is desired to prepare a compound of the formula (I) from another compound of formula (I) wherein $R^7$ is hydrogen, by reaction of the anion from such a compound with an alkylating agent $halR^7$, wherein hal is halogen and $R^7$ is other than hydrogen. This reaction is particularly suitable for the preparation of those compounds wherein $R^7$ is a $C_{1-4}$ alkyl group or a group $COR^{23}$ wherein $R^{23}$ is a $C_{1-4}$ alkoxy group. The reaction is normally carried out in the presence of a strong base, such as an alkyllithium conveniently butyllithium in an inert solvent, such as an ether, for example tetrahydrofuran, at a non-extreme temperature, for example between $-50°$ and 50° C. and conveniently between $-10°$ and 30°. The starting material. e.g. an unsubstituted alkynyl oxathiane, may be prepared as described above.

(b) when it is desired to prepare a compound of the formula (I) wherein $R^7$ is hydrogen by the desilylation of a compound of the formula (I) wherein $R^7$ is a tri-$C_{1-4}$ alkylsilyl group. This reaction may be carried out by methods well known to those skilled in the art, for example by reaction with tetrabutylammonium fluoride in an ether, such as tetrahydrofuran, at a non-extreme temperature, for example between 0° and 70° C. and conveniently at room temperature.

(c) The compounds of the formula (I) contain a minimum of one and a maximum of three sulphur atoms which may be oxidised if required. Oxidations can be carried out by methods well known to those skilled in the art, for example using peracids such as peracetic acid from hydrogen peroxide and acetic acid, or 3-chloroperbenzoic acid in chloroform or dichloromethane, or using periodate such as tetrabutylammonium periodate in a halogenated hydrocarbon, for example chloroform at a non-extreme temperature, for example between 0° and 100° C. and conveniently between 10° and 30° C.

The compounds of formula (I) may be used to control pests such as arthropods, e.g. insect and acarine pests, and helminths, e.g. nematodes. Thus, the present invention provides a method for the control of arthropods and/or helminths which comprises administering to the arthropod and/or helminth or to their environment an effective amount of a compound of the formula (I). The present invention also provides a method for the control of arthropod and/or helminth infestations of animals (including humans) and/or of plants (including trees) and/or stored products which comprises administering an effective amount of a compound of the formula (I). The present invention further provides for the compounds of the formula (I) for use in human and veterinary medicine, in public health control and in agriculture for the control of arthropod and/or helminth pests.

By the term "control" is meant the amelioration in air, water, soil or foliage of present or future deleterious effects of pests and includes killing adults, larvae and eggs, the inhibition of reproduction, the repellency and/or knockdown of pests, and any other influence on behaviour.

Compounds of formula (I) are of particular value in the protection of field, forage, plantation, glasshouse, orchard and vineyard crops, of ornamentals and of plantation and forest trees, for example, cereals (such as maize, wheat, rice, millet, oats, barley, sorghum), cotton, tobacco, vegetables and salads (such as beans, cole crops, cucurbits, lettuce, onions, tomatoes and peppers), field crops (such as potato, sugar beet, ground nuts, soyabean, oil seed rape), sugar cane, grassland and forage crops (such as lucerne), plantations (such as of tea, coffee, cocoa, banana, oil palm, coconut, rubber, spices), orchards and groves (such as of stone and pip fruit, citrus fruits, kiwifruit, avocado, mango, olives and walnuts), vineyards, ornamental plants, flowers and shrubs under glass and in gardens and parks, forest trees (both deciduous and evergreen) in forests, plantations and nurseries and plants grown for industrial or pharmaceutical purposes (such as the evening primrose).

They are also valuable in the protection of timber (standing, felled, converted, stored or structural) from attack by sawflies (e.g. Urocerus) or beetles (e.g. scolytids, platypodids, lyctids, bostrychids, cerambycids, anobiids) termites (e.g. Isoptera) or other damaging pests.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

Compounds of formula (I) are of value in the control of public health pests, for example cockroaches and ants.

Compounds of formula I are also of value in the control of arthropods or helminths which are injurious to, or spread or act as vectors of diseases in man and domestic animals, for example those hereinbefore mentioned, and more especially in the control of ticks, mites, lice, fleas, midges biting, nuisance and myiasis flies, mosquitoes and hemipteran bugs.

The compounds of Formula (1) may be used for such purposes by application of the compounds themselves or in diluted form in known fashion as a dip, spray, fog, lacquer, foam, dust, powder, aqueous suspension, paste, gel, cream, shampoo, grease, combustible solid, vapourising mat, combustible coil, bait, dietary supplement, wettable powder, granule, aerosol, emulsifiable concentrate, oil suspension, oil solution, pressure-pack, impregnated article, microcapsule, pour on formulation or other standard formulations well known to those skilled in the art. Sprays may be applied by hand or by means of a spray race or arch or by vehicle or aircraft mounted apparatus. The animal, soil, plant or other surface being treated may be saturated with the spray by means of high volume application or superficially coated with the spray by means of light or ultra low volume application. Dip concentrates are not applied per se, but diluted with water and the animals immersed in a dipping bath containing the dip wash. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

Compounds of Formula (I) may be prepared either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powders and granules and other solid formulations comprise the compound of formula (I) in intimate admixture with a powdered solid inert carrier for example suitable clays, kaolin, bentonite, attapulgite, adsorbent carbon black, talc, mica, silica, chalk, gypsum, tricalcium phosphate, powdered cork, magnesium silicate, vegetable carriers, starch or a diatomaceous earth. Such solid formulations are generally prepared by impregnating the solid diluents with solutions of the compound of formula (I) in volatile solvents, evaporating the solvents and, if desired, grinding the products so as to obtain powders and, if desired, granulating, compacting or encapsulating the products.

Sprays of a compound of Formula (1) may comprise a solution in an organic solvent (e.g. those listed below)

or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 99.5% w/v of the composition and may be selected from kerosene, ketones, alcohols, xylene, aromatic naphtha, water, mineral oil, aromatic and aliphatic esters, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates, soaps, lecithins, hydrolysed glues, etc.

Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, or other solvents known in the art.

Wettable powders and emulsifiable concentrates will normally contain from 0.5 to 99.5% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution, they should contain the appropriate percentage of the compound of Formula (I) required for treatment.

Aerosol sprays may be prepared as a simple solution of the active ingredient in the aerosol propellant and co-solvent such as halogenated alkanes, propane, butane, dimethyl ether and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is polyvinyl chloride (PVC).

The concentration of the compound of formula (I) to be applied to an animal, premises, other substrates or outdoor areas will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited will vary according to the compound chosen, the method of application, area of application, concentration of the compound in the applied formulation, factor by which the formulation is diluted and the nature of the formulation.

Undiluted formulations such as pour-on formulations in general will be applied at a concentration in the range from 0.1 to 20.0% w/w and preferably 0.1 to 10%. The amount of compound to be applied to stored products in general will lie in the range of from 0.1 to 20 ppm. Space sprays may be applied to give an average initial concentration of 0.001 to 1 mg of compound of formula (1) per cubic meter of treated space.

Compounds of formula (I) are of use in the protection and treatment of plant species, in which case an effective insecticidal, acaricidal or nematocidal amount of the active ingredient is applied to the plant or the medium in which the plant is grown. The application rate will vary according to the compound chosen, the nature of the formulation, the mode of application, the plant species, the planting density and likely infestation and other like factors but in general, a suitable use rate for agricultural crops is in the range 0.001 to 3kg/Ha and preferably between 0.01 and 1kg/Ha. Typical formulations for agricultural use contain between 0.0001% and 50% of a compound of formula (I) and conveniently between 0.1 and 15% by weight of a compound of the formula (I).

Dusts, greases, pastes and aerosol formulations are usually applied in a random fashion as described above and concentrations of 0.001 to 20% w/v of a compound of Formula (1) in the applied formulation may be used.

The compounds of formula (I) have been found to have activity against the common housefly (*Musca domestica*). In addition, certain compounds of formula (I) have activity against other arthropod pests such as *Myzus persicae, Tetranychus urticae, Plutella xylostella, Culex* spp. *Tribolium castaneum, Sitophilus granarius, Periplaneta americana* and *Blattella germanica*. The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium, Ceutorhynchus, Rhynchophorus, Cosmopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus or Anthrenus spp.), Lepidoptera (e.g. Ephestia, Mamestra, Earias, Pectinophora, Ostrinia, Trichoplusia, Pieris, Laphyoma, Agrotis, Amathes, Wiseana, Tryporyza, Diatraea, Sporganothis, Cydia, Archips, Plutella, Chilo, Heliothis, Spodoptera or Tineola spp.), Diptera (e.g. Musca, Aedes, Anopheles, Culex, Glossina, Simulium, Stomoxys, Haematobia, Tabanus, Hydrotaea, Lucilia, Chrysomia, Callitroga, Dermatobia, Gasterophilus, Hypoderma, Hylemyia, Atherigona, Chlorops, Phytomyza, Ceratitis, Liriomyza and Melophagus spp.), Phthiraptera (Malophaga e.g. Damalina spp. and Anoplura e.g. Linognathus and Haematopinus spp.), Hemiptera (e.g. Aphis, Bemisia, Phorodon, Aeneolamia, Empoasca, Parkinsiella, Pyrilla, Aonidiella, Coccus, Pseudococcus, Helopeltis, Lyous, Dysdercus, Oxycarenus, Nezara, Aleurodes, Triatoma, Rhodnius, Psylla, Myzus, Megoura, Phylloxera, Adelyes, Niloparvata, Nephrotettix or Cimex spp.), Orthoptera (e.g. Locusta, Gryllus, Schistocerca or Acheta spp.), Dictyoptera (e.g. Blattella, Periolaneta or Blatta spp.), Hymenoptera (e.g. Athalia, Cephus, Atta Lasius, Solenopsis or Monomorium spp.), Isoptera (e.g. Odontotermes and Reticulitermes spp.), Siphonaptera (e.g. Ctenoceohalides or Pulex spp.), Thysanura (e.g. Leoisma spp.), Dermaptera (e.g. Forficula spp.), Psocoptera (e.g. Periosocus spp.) and Thysanoptera (e.g. *Thrips tabaci*).

Acarine pests include ticks, e.g. members of the genera Boophilus, Ornithodorus, Rhipicephalus, Amblyomma, Hyalomma, Ixodes, Haemaphysalis, Dermacentor and Anocentor, and mites and manges such as Acarus, Tetranychus, Psoroptes, Notoednes, Sarcoptes, Psorergates, Chorioptes, Eutrombicula, Demodex, Panonychus, Bryobia and Eriophyes spp.

Nematodes which attack plants and trees of importance to agriculture, forestry, horticulture, either directly or by spreading bacterial, viral, mycoplasma or fungal diseases of the plants, include root-knot nematodes such as Meloidogyne spp. (e.g. *M. incognita*); cyst nematodes such as Globodera spp. (e.g. *G. rostochiensis*); Heterodera spp. (e.g. *H. avenae*): Radopholus spp. (e.g. *R. Similis*); lesion nematodes such as Pratylenchus spp. (e.g. *P. oratensis*); Belonolaimus spp. (e.g. *B. oracilis*); Tylenchulus spp. (e.g. *T. semipenetrans*): Rotylenchulus spp. (e.g. *R. reniformis*); Rotylenchus spp. (e.g. *R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T primitivus*): dagger nematodes such as Xiphinema spp. (e.g. *X. diversicaudatum*), Longidorus spp (e.g. *L. elongatusl*); Hoplolaimus spp. (e.g. *H. coronatus*); Aphelenchoides spp. (e.g. *A. ritzema-bosi, A. besseyi*): stem and bulb eelworms such as Ditylenchus spp. (e.g. *D. diosaci*).

Compounds of the invention may be combined with one or more other pesticidally active ingredients (for example pyrethroids, carbamates, lipid amides and organophosphates) and/or with attractants, repellents, bacteriocides, fungicides, anthelmintics and the like. Furthermore, the activity of compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synergist is present in a formulation of the invention, the ratio of synergist to compound of Formula (I) will be in the range 500:1-1:25 eg about 100:1 to 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilisers and as scavengers.

EXAMPLE 1

5-t-Butyl-2-(4-ethynylphenyl)-1,3-oxathiane i) A mixture of 2-t-butylpropane-1,3-diol (11.0 g.) (E.L. Eliel et al *J. Amer Chem Soc.* 1968, 90, 3444) was stirred in dry toluene (200 ml), at 20° C. Sodium hydride (2.4 g., 80% dispersion in oil), previously washed with hexane, was added carefully to the stirred mixture. The mixture was stirred at 120° C. for 30 minutes and cooled. Benzyl bromide (9.5 ml) was added dropwise and the mixture heated at 130°, with stirring for 6 hours. The mixture was cooled, water was added and the mixture extracted with diethyl ether. The ethereal extracts were washed with water, dried over anhydrous magnesium sulphate and evaporated in vacuo. The residue was purified by chromatography on silica, eluting with 1:4 diethyl ether: hexane. 2-Benzyloxymethyl-3,3-dimethylbutan-1-ol (8.0 g) was obtained as a colourless ii) 2-Benzyloxymethyl-3,3-dimethylbutan-1-ol (5.8 g) in dry pyridine (20 ml) was stirred at 0° C. Then methanesulphonyl chloride (3.5 g) was added dropwise and the mixture was stirred at 0.C. for 3 hours and at 20° C. for 5 hours. Water was added and the aqueous mixture was extracted with diethyl ether. The ethereal extracts were washed with water, dried over anhydrous magnesium sulphate and evaporated in vacuo. .

2-Benzyloxymethyl-3,3-dimethylbut-1-yl methanesulphonate was obtained as a yellow oil (7.3 g) and was used without further purification.

iii) Benzyl mercaptan (3.1 ml) was stirred in dry dimethylformamide (100 ml), at 0°, under a current of nitrogen. Sodium hydride (0.75 g., 80% dispersion in oil), previously washed with hexane, was added carefully and the mixture was stirred at 0° C. for 30 minutes. 2-Benzyloxymethyl-3,3-dimethylbut-1-yl methanesulphonate (7.3 g), in dry dimethylformamide (20 ml) was added and the mixture was stirred at 100° for 3 hours. The mixture was cooled and water was added. The aqueous mixture was extracted with diethyl ether. The ethereal extracts were washed with water, dried over anhydrous magnesium sulphate and evaporated in vacuo. The residue was purified by chromatography on silica, eluting with 1:4 diethyl ether: hexane. 2-Benzylthiomethyl-3,3-dimethylbutyl benzyl ether was obtained as a colourless oil (7.0 g).

iv) Anhydrous liquid ammonia (400 ml) was stirred at −70°, under a current of nitrogen. 2-Benzylthiomethyl-3,3-dimethylbutyl benzyl ether (7.0 g) in dry diethyl ether (100 ml) was added and this was followed by sodium (4.0 g) in small pieces. The resulting mixture was stirred at −70° for 3 hours and then allowed to warm up to 20° C. Ammonium chloride (20 g) was added followed by dry methanol (70 ml). When all the sodium had dissolved, water was added and the mixture was extracted with diethyl ether. The ethereal extracts were washed with water, dried over anhydrous magnesium sulphate and evaporated in vacuo. 3,3-Dimethyl-2-mercaptomethyl-butan-1-ol was obtained as a pale yellow oil (2.8 without further purification.

v) A solution of 3,3-dimethyl-2-mercaptomethylbutan-1-ol (1.46 g), 4-ethynylbenzaldehyde (1.30 g) (W.B. Austin et al. J. Org. Chem., 1981, 46. 2280) and para-toluenesulphonic acid (10 mg) in benzene (50 ml) was heated to reflux overnight under Dean and Stark conditions. The resulting solution was evaporated under reduced pressure and the residue was purified on silica. Elution with 4:1 hexane: dichloromethane gave 5-t-butyl-2-(4-ethynylphenyl)-1,3-oxathiane as a mixture of isomers.

Recrystallisation from hexane afforded the trans-isomer (5(e)-t-butyl-2(e)-(4-ethynylphenyl)-1,3-oxathiane) as a white solid.

Evaporation of the mother liquors gave an enriched mixture of the cis-and trans-isomers.

EXAMPLE 2

5(e)-t-Butyl-2(e)-(4-ethynylphenyl)-1.3-oxathiane 3-oxide

A solution of trans-5-t-butyl-2-(4-ethynylphenyl)-1,3-oxathiane (520 mg) and m-chloroperbenzoic acid (90%, 400 mg. 1 equivalent) in dry dichloromethane (35 ml) was stirred at room temperature overnight. The solution was washed with pH 8.0 sodium phosphate buffer, dried over anhydrous magnesium sulphate and evaporated under reduced pressure. Purification on silica, eluting with chloroform, followed by recrystallisation from hexane-dichloromethane gave the title compound as a mixture of two oxides (500 mg).

EXAMPLE 3

5(e)-t-Butyl-2(e)-(4-ethynylphenyl)-1.3-oxathiane 3,3-dioxide

A solution of 5(e)-t-butyl-2(e)-(4-ethynylphenyl)-1,3-oxathiane (520 mg) and m-chloroperbenzoic acid (90%) (1.0 g, 3 equivalents) in dry dichloromethane (35 ml) was stirred at room temperature overnight. The solution was washed with pH 8.0 sodium phosphate buffer, dried (MgSO4) and evaporated. Purification on a silica column eluting with hexane/dichloromethane (2:3) gave the dioxide (540 mg) as white needles.

EXAMPLE 4

Trans-5(e)-(t-butyl-2(e)-(hex-5-ynyl)-1,3-oxathiane i) To a stirred solution of oxalyl chloride (1.9 ml) in dry dichloromethane (20 ml) at −70° under a nitrogen atmosphere, was added a solution of dimethylsulphoxide (1.67 g) in dichloromethane (10 ml) dropwise. The resulting mixture was maintained at −70 for 10 minutes when a solution of hept-6-yn-1-ol (C.Crisan Chem. Abs. 51: 50615) (1.6 g) in dichloromethane (10 ml) was added. After a further hour at −70°, triethylamine (9.7 mls) was added and the reaction was allowed to warm to room temperature overnight. After this time the reaction mixture was washed with water, dilute hydrochloric acid and saturated sodium bicarbonate solution before drying over anhydrous magnesium sulphate. Evaporation of the solvent gave hept-6-ynal (1.2 g) which was used without further purification.

ii) Using the method described in Example 1(v), trans-5(e)-t-butyl -2(e)-(hex-5-ynyl)-1,3-oxathiane was prepared from 3,3-dimethyl -2-mercaptomethylbutan-1-ol and hept-6-ynal.

EXAMPLE 5

2-(hex-5-ynyl)-5-isopropyl-1,3-oxathiane i) A solution of diethyl isopropylmalonate (17 g) in dry diethyl ether (20 ml) was added dropwise to a stirred suspension of lithium aluminium hydride (7 g) in ether (300 ml) at 0° under nitrogen. The resulting mixture was stirred at room temperature for 8 hours when 10% aqueous sodium hydroxide solution (30 ml) was added carefully. The mixture was then filtered and the solid residue washed through with fresh diethyl ether. The combined filtrates were dried over anhydrous magnesium sulphate and then evaporated in vacuo to leave 2-isopropylpropane-1,3-diol as a colourless oil (8.9 g).

ii) A solution of hydrobromic acid in acetic acid (30%, 0.5 ml) was added to a solution of 2-isopropylpropane-1,3-diol (10 g) in glacial acetic acid (20 ml) and the mixture heated to reflux for 20 minutes. A further portion of 30% hydrobromic acid in acetic acid (26 ml) was then added dropwise and the resulting mixture maintained at reflux for a further 6 hours. The solvent was then removed in vacuo, and residues removed by azeotroping with hexane, to leave 2-bromomethyl-3-methylbutyl acetate (15 g) which was used without further purification.

iii) A mixture of 2-bromomethyl-3-methylbutyl acetate (6 g) and potassium thiocyanate (7.3 g) in dry dimethylformamide (50 ml) was heated at 140° for 2 hours. After cooling, the reaction mixture was poured into water (150 ml) and then extracted with diethylether (3×50 ml). The combined ethereal extracts were washed with water (3×50 ml) before drying over anhydrous magnesium sulphate and evaporation in vacuo. 2-Thiocyanatomethyl-3methylbutyl acetate was obtained and was used without further purification.

iv) A mixture of 2-thiocyanatomethyl-3-methylbutyl acetate (3.5 g) and sodium hydroxide in ethanol (30 ml) and water (60 ml) was heated to reflux under nitrogen for 2 hours. After allowing to cool, the reaction mixture was poured into saturated ammonium chloride solution (200 ml) and then extracted with ether (4×50 ml). The combined ethereal extracts were washed with water, dried over anhydrous magnesium sulphate and then evaporated in vacuo to give 2-mercaptomethyl-3-methylbutan-1-ol (1.9 g).

In a similar manner and starting from diethyl phenylmalonate, 2-mercaptomethyl-2-phenylethanol was prepared.

v) Using the method described in Example 4(ii), and starting from 2-mercaptomethyl-3-methylbutan-1-ol and hept-6-ynal, 2-(hex-5-ynyl)-5-isopropyl-1,3-oxathiane was obtained as a mixture of isomers. Column chromatography on silica, eluting with hexane/ether gradients, gave a mixture of trans-and cis-isomers (50:50) followed by an enriched mixture of the trans-compound (95:5).

EXAMPLE 6

2-(4-ethynylcyclohexyl)-5-isopropyl-1,3-oxathiane

Using the method described in Example 1(v) and starting from 4-ethynyl cyclohexanecarboxaldehyde (European Patent Application No. 88305107) and 2-mercaptomethyl-3-methylbutan-1-ol, 2-(4-ethynylcyclohexyl)-5-isopropyl-1,3-oxathiane was obtained as a mixture of isomers.

EXAMPLE 7

5(e)-t-Butyl-2(e)-6(e)-methyl(4-trimethylsilylethynylphenyl)-1,3-oxathiane i) Using the method described in Example 5(ii) and starting from 2-t-butylpropane-1,3-diol, 2-bromomethyl-3,3-dimethylbutyl acetate was prepared.

ii) Sodium hydride (2 g; 80%) was added to a stirred solution of benzyl mercaptan (9.4 g) in dry dimethylformamide (100 ml) at room temperature under a nitrogen atmosphere. The resulting mixture was heated at reflux for 1 hour when a solution of 2-bromomethyl-3,3-dimethylbutyl acetate (13.3 g) in DMF (10 ml) was added. After a further hour at reflux, the mixture was allowed to cool and then poured into water (300 ml). The aqueous mixture was extracted with ether and then the combined ethereal extracts were washed with water before drying over anhydrous magnesium sulphate and evaporation in vacuo. The resulting residue was taken up in a mixture of 10% aqueous potassium hydroxide and ethanol (1:1, 50 ml) and heated to reflux for 1 hour. After cooling, the aqueous solution was exhaustively extracted with ether. The combined ethereal extracts were dried over anhydrous magnesium sulphate and then evaporated in vacuo. The residue was purified by column chromatography on silica. Gradient elution with hexane/diethylether mixtures gave 2-benzylthiomethyl-3,3-dimethylbutanol as an oil (4.5 g).

iii) A solution of 2-benzylthiomethyl-3,3-dimethylbutanol (3.7 g) in dry dichloromethane (15 ml) was added to a mechanically stirred suspension of pyridinium chlorochromate (10 g) and sodium acetate (1 g) in dichloromethane (100 ml) at 0° C. The resulting mixture was stirred at room temperature for two hours and then diethylether (300 ml) was added. The reaction mixture was passed through a short column of silica and charcoal (1:1) and then evaporated in vacuo to leave 2-benzylthiomethyl-3,3-dimethylbutanal as an oil (1.42 g).

iv) A solution of methylmagnesium bromide in diethylether (20 ml) was prepared from magnesium (0.16 g) and bromomethane (0.63 g). A solution of 2-benzylthiomethyl-3,3-dimethylbutanal (1.42 g) in ether (5 ml) was then added and the resulting mixture was heated under reflux for 20 minutes and then allowed to stir at room temperature overnight. After this time, dilute hydrochloric acid (10 ml) was added and the organic phase separated and washed with saturated sodium bicarbonate and brine before drying over anhydrous magnesium sulphate and evaporation in vacuo. The crude product was purified by column chromatography on silica, eluting with hexane/diethylether mixtures to leave 2-benzylthio-methyl-1,3,3-trimethylbutanal as an oil (0.75 g).

v) Using the method described in Example 1(iv), 2-benzylthiomethyl-1,3,3-trimethylbutanol was converted to 2-mercaptomethyl-1,3,3-trimethylbutanol.

vi) Using the method described in Example 1(v) and starting from 2-mercaptomethyl-1,3,3-trimethylbutanol and 4-trimethylsilylethynylbenzaldehyde (W.B.Austin et al. *J. Org.Chem.*, 1981, 46, 2280), 5(e)-t-butyl-2(e)-(4-trimethylsilylethynylphenyl)-6-methyl-1,3-oxathiane was obtained as a mixture of isomers. Column chromatography on silica and eluting with hexane/2% ether gave 5(e)-t-butyl-2(e)-6(e)-methyl(4-trimethylsilylethynylphenyl)-1,3-oxathiane as a white solid.

EXAMPLE 8

5(e)-t-Butyl-2(e)-(4-ethynylphenyl)-6(e)-methyl-1,3-oxathiane and
5(e]-t-butyl-2(e)-(4-ethynylphenyl)-6(a)methyl-1,3-oxathiane An isomeric mixture of 5(e)-t-butyl-2(e)-6-methyl(4-trimethylsilyl-ethynylphenyl)-1,3-oxathiane (0.6 g) (10 ml) and a solution of tetra-n-butylammonium fluoride in THF (IM, 2.5 ml) added. The resulting mixture was stirred at room temperature overnight. After this time water (5 ml) was added and the bulk of the THF was removed in vacuo. The residue was extracted with ether and the combined ethereal extracts were washed with brine and then dried over anhydrous magnesium sulphate before evaporation in vacuo. The residue was purified by column chromatography on silica, eluting with hexane/2.5% ether to give the title compounds as a mixture of isomers. (0.12 g).

EXAMPLE 9 trans-5(e)-t-Butyl-2(e)-(4-ethynyl-3-fluorophenyl)-1,3-oxathiane i) A mixture of acetic acid (108 ml), acetic anhydride (0.58 ml) and 4-bromo-3-fluorotoluene (20 g) was cooled to -10° when concentrated sulphuric acid (22.5 mls) was added dropwise, such that the temperature did not exceed −5°. When the addition was complete, chromium trioxide (31.3 g) was added portionwise at such a rate that the temperature did not exceed 5°. The resulting mixture was stirred for 30 minutes and then poured onto ice (300 g). The reaction mixture was then extracted with diethyl ether and the combined ethereal extracts were washed with 2M sodium hydroxide and brine before drying over anhydrous magnesium sulphate and evaporation in vacuo. Recrystallisation from hexane gave 4-bromo-3-fluorobenzylidene diacetate (15 g).

ii) A mixture of 4-bromo-3-fluorobenzylidene diacetate (15 g), ethanol (41 ml), water (41 ml) and concentrated sulphuric acid (4 ml) was heated to reflux for 3 hours. After cooling, ether (300 ml) was added and the aqueous layer separated. The organic phase was washed with saturated sodium carbonate and brine before drying over anhydrous magnesium sulphate and evaporation in vacuo. 4-Bromo-3-fluorobenzaldehyde was obtained as a solid (7.3 g).

iii) To a stirred solution of 4-bromo-3-fluorobenzaldehyde (6 g) in triethylamine (60 ml) was added trimethylsilylacetylene (4.6 ml), bis-triphenylphosphinepalladium dichloride (331 mg) and cuprous iodide (130 mg). The resulting mixture was allowed to stir overnight at room temperature under a nitrogen atmosphere. After this time, diethyl ether was added and the mixture was filtered. The filtrate was washed with water and brine before drying over anhydrous magnesium sulphate and evaporation in vacuo. The resulting oil was crystallised from cold hexane to give 3-fluoro-4-trimethylsilylethynylbenzaldehyde as a light brown solid (4 g).

iv) Using the method described in Example 1(v) and starting from 3-fluoro-4-trimethylsilylethynylbenzaldehyde and 3,3-dimethyl-2-mercaptomethylbutan-1-ol, trans-5(e)-t-butyl-2(e)-(3-fluoro-4-trimethylsilylethynylphenyl)-1,3-oxathiane was prepared.

v) Using the method described in Example 8, trans-5(e)-t-butyl-2(e)-(3-fluoro-4-trimethylsilylethynylphenyl)-1,3-oxathiane was converted to trans-5(e)-t-butyl-2(e)-(4-ethynyl-3-fluorophenyl)-1,3-oxathiane.

TABLE 1.

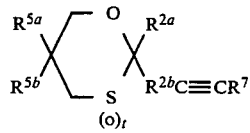

| Compound Number | Isomer | $R^{2b}C{\equiv}CR^7$ | $R^{2a}$ | $R^{5a}$ | $R^{5b}$ | Isomer Ratio | t |
|---|---|---|---|---|---|---|---|
| 1. | trans | 4-ethynylphenyl | H | tert-butyl | H | — | 0 |
| 2. | trans | 4-ethynylphenyl | H | tert-butyl | H | Mixture | 0 |
|  | cis | 4-ethynyl phenyl | H |  | H |  |  |
| 3. | trans | 4-ethynylphenyl | H | tert-butyl | H | Mixture | 1 |
| 4. | trans | 4-ethynylphenyl | H | tert-butyl | H | — | 2 |
| 5. | trans | hex-5-ynyl | H | tert-butyl | H | — | 0 |
| 6. | trans | hex-5-ynyl | H | tert-butyl | H | — | 2 |
| 7. | trans | hex-5-ynyl | H | isopropyl | H | 1 | 0 |
|  | cis | hex-5-ynyl | H | isopropyl | H | 1 |  |
| 8. | trans | hex-5-ynyl | H |  | H | 9.5 | 0 |
|  | cis | hex-5-ynyl | H | isopropyl | H | 0.5 |  |
| 9. | trans | hex-5-ynyl | H | isopropyl | H | — | 2 |
| 10. | trans | hex-5-ynyl | H | isopropyl | H | 1 | 2 |
|  | cis | hex-5-ynyl | H | isopropyl | H | 3 |  |
| 11. | trans | 4-ethynylcyclohexyl | H | isopropyl | H | 2 | 0 |
|  | cis | 4-ethynylcyclohexyl | H | isopropyl | H | 1 |  |
| 12 | trans | 4-ethynylcyclohexyl | H | isopropyl | H | 4 | 0 |
|  | cis | 4-ethynylcyclohexyl | H | isopropyl | H | 1 |  |
| 13. | trans | 4-ethynylphenyl | H | isopropyl | H | — | 2 |
| 14. | trans | 4-ethynylphenyl | H | isopropyl | H | — | 1 |
| 15. | cis | 4-ethynylphenyl | H | isopropyl | H | — | 1 |
| 16. | trans | 4-ethynylphenyl | H | phenyl | H | — | 0 |
| 17. | trans | 4-ethynylphenyl | H | phenyl | H | — | 2 |
| 18. | trans | hex-5-ynyl | H | phenyl | H | 9 | 0 |
|  | cis | hex-5-ynyl | H | phenyl | H | 1 |  |
| 19. | trans | hex-5-ynyl | H | phenyl | H | — | 2 |
| 20. | trans | 4-ethynyl-3-fluoro-phenyl | H | tert-butyl | H | — | 0 |
| 21 | trans | 4-ethynylcyclohexyl | H | tert-butyl | H | 5 | 0 |
|  | cis | 4-ethynylcyclohexyl | H | tert-butyl | H | 1 |  |

TABLE 2

Nuclear Magnetic Resonance Spectra: $^1$H, $CDCl_3$, expressed as ppm downfield from TMS (number of protons, multiplicity).

| Compound Number. | |
|---|---|
| 1. | 0.95(9H, s), 1.70(1H, dt), 2.85(1H, dt), 3.00(1H, dd), 3.05(1H, s), 3.55(1H, dd), 4.40(1H, ddd), 5.65(1H, s), 7.40(2H, d), 7.45(2H, d). |
| 2. | trans. 0.95(9H, s), 1.70(1H, dt), 2.85(1H, dt), 3.00(1H, dd), 3.05(1H, s), 3.55(1H, dd), 4.40(1H, ddd), 5.65(1H, s), 7.40(2H, d), 7.45(2H, d). |
|  | cis. 1.00(9H, s), 1.60(1H, m), 2.80(1H, dd), 2.95(1H, dd), 3.10(1H, s), 3.85(1H, dd), 4.00(1H, dd), 5.80(1H, s), 7.50(4H, s). |
| 3. | Major Isomer. 1.00(9H, s), 2.00(1H, m), 2.70(1H, dd), 3.10(1H, s), 3.60(1H, dd), 3.70(1H, dt), 4.30(1H, ddd), 4.80(1H, s), 7.45(2H, d), 7.50(2H, d). |
|  | Minor Isomer. 0.95(9H, s), 2.50(1H, m), 2.65(1H, dd), 3.05(1H, s), 3.35(1H, dt), 3.70(1H, dd), 4.45(1H, dd), 5.15(1H, s), 7.40(2H, d), 7.5(2H, d). |
| 4. | 1.00(9H, s), 2.5(1H, m), 3.05(1H, dd), 3.10(1H, s), 3.40(1H, dt), 3.65(1H, dd), 4.45(1H, ddd), 5.30(1H, s), 7.45(2H, d), 7.55(2H, d). |
| 5. | 0.87(9H, s), 1.4–1.85(7H, m), 1.92(1H, t), 2.15(2H, m), 2.77(2H, m), 3.35(1H, dd), 4.23(1H, m), 4.60(1H, dd). |
| 6. | 0.90(9H, s), 1.45–2.4(10H, m), 2.84(1H, dd), 3.25(1H, m), 3.45(1H, dd), 4.15–4.35(2H, m). |
| 7, 8. | trans 0.87(6H, d), 1.3–1.85(8H, m), 1.96(1H, t), 2.15(2H, m), 2.75(2H, m), 3.27(1H, dd), 4.13(1H, m), 4.62(1H, dd). |
|  | cis 0.95(6H, m), 1.3–1.85(7H, m), 1.96(1H, t), 2.15(2H, m), 2.36(1H, m), 2.80(1H, m), 3.08(1H, dd), 3.57(1H, dd), 4.13(1H, m), 4.72(1H, dd). |
| 9, 10. | trans 0.90(6H, m), 1.4–1.85(6H, m), 1.88–2.08(2H, m), 2.18(2H, m), 2.35(1H, m), 2.82(1H, dd), 3.20(1H, m), 3.40(1H, dd), 4.15(1H, m), 4.22(1H, dd). |
|  | cis 0.95(6H, m), 1.45–2.1(9H, m), 2.18(2H, m), 3.08(1H, dd), 3.21(1H, m), 3.75(1H, dd), 3.94(1H, dd), 4.35(1H, m). |
| 11, 12. | 0.9–2.2 and 2.35(19H, m), 2.6–2.9(2H, m), 3.05, 3.25, 3.55 and 4.15(2H, m), 4.46 and 4.60(1H, m). |
| 13. | 0.95(3H, d), 0.99(3H, d), 1.67(1H, m), 2.55(1H, m), 3.02(1H, dd), 3.10(1H, s), 3.36(1H, m), |

TABLE 2-continued

Nuclear Magnetic Resonance Spectra: $^1$H, CDCl$_3$, expressed as ppm downfield from TMS (number of protons, multiplicity).

| Compound Number. | |
|---|---|
| | 3.64(1H, dd), 4.35(1H, m), 5.30(1H, s), 7.55(4H, m). |
| 14. | 0.98(6H, d), 1.70(1H, m), 2.05(1H, m), 2.66(1H, dd), 3.08(1H, s), 3.54(1H, dd), 3.65(1H, m), 4.23(1H, m), 4.85(1H, s), 7.48(4H, m). |
| 15. | 1.03(3H, d), 1.10(3H, d), 1.87(1H, m), 2.01(1H, m), 2.90(1H, dd), 3.08(1H, s), 3.67(1H, m), 3.88(1H, dd), 4.28(1H, m), 4.88(1H, s), 7.48(4H, m). |
| 16. | 2.97(1H, m), 3.10(1H, s), 3.29(1H, m), 3.44(1H, m), 3.82(1H, m), 4.34(1H, m), 5.87(1H, s), 7.2-7.6(9H, m). |
| 17. | 3.15(1H, s), 3.56(2H, m), 3.95(2H, m), 4.40(1H, m), 5.55(1H, s), 7.2-7.7(9H, m). |
| 18. | trans 1.45-2.05(7H, m), 2.22(2H, m), 2.90(1H, m), 3.15(1H, m), 3.25(1H, m), 3.65(1H, m), 4.16(1H, m), 4.85(1H, m), 7.15-7.50(5H, m). |
| | cis 1.45-2.05(7H, m), 2.35(2H, m), 2.95(1H, m), 3.10(1H, m), 3.46(1H, m), 4.0(1H, m), 4.35(1H, m) 4.88(1H, m), 7.15-7.50(5H, m). |
| 19. | 1.5-2.2(7H, m), 2.25(2H, m), 3.44(2H, m), 3.65-3.90(2H, m), 4.23(1H, m), 4.45(1H, m), 7.15-7.45(5H, m). |
| 20. | 0.96(9H, s), 1.85(1H, m), 2.90(1H, m), 3.01(1H, m), 3.30(1H, s), 3.57(1H, m), 4.45(1H, m), 5.69(1H, s), 7.25(2H, m), 7.45(1H, m). |
| 21. | 0.95(9H, s), 1.0-2.1(11H, m), 2.17(1H, m), 2.7-2.95(2H, m), 3.36 and 4.25(2H, m), 4.46 and 4.53(1H, m). |
| 22. | 0.25(9H, s), 1.0(9H, s), 1.45(3H, d), 1.55(1H, m), 2.92(2H, m), 3.65(1H, m), 5.72(1H, s), 7.40(4H, m). |
| 23. | 1.0 and 1.05(9H, s), 1.45(3H, d), 1.55(1H, m), 2.85-3.15(3H, m), 3.65 and 4.40(1H, m), 5.75 and 5.95(1H, s), 7.45(4H, m). |
| 24. | 1.05(9H, s), 1.55(3H, d), 2.32(1H, m), 3.05(1H, m), 3.15(1H, s), 3.40(1H, m), 3.90(1H, m), 5.43(1H, m), 7.55(4H, m). |
| 25. | 1.05(9H, s), 1.55(3H, d), 2.12(1H, m), 3.10(1H, s), 3.16(1H, m), 3.35(1H, m), 4.25(1H, m), 5.70(1H, s), 7.50(4H, m). |

TABLE 3

Further Characterising Data.

| Compound Number | Mass Spectrum Chemical Ionisation (M + 1) | M.p. °C. | Description | Method of Synthesis |
|---|---|---|---|---|
| 1. | 261 | 117-119° | White solid | Example 1 |
| 2. | 261 | | White solid | Example 1 |
| 3. | 277 | 128-130° | White solid | Example 2 |
| 4. | 293 | 204-206° | White solid | Example 3 |
| 5. | 241 | — | oil | Example 4 |
| 6. | 290(M + 18) | 107-8° | White solid | Example 3 |
| 7. | 227 | — | oil | Example 5 |
| 8. | 227 | — | oil | Example 5 |
| 9. | 276(M + 18) | — | oil | Example 3 |
| 10. | 276(M + 18) | — | oil | Example 3 |
| 11. | 253 | — | oil | Example 6 |
| 12. | 253 | — | oil | Example 6 |
| 13. | 279 | 178° | White solid | Example 3 |
| 14. | 263 | 112° | White solid | Example 2 |
| 15. | 263 | 83° | White solid | Example 2 |
| 16. | 281 | 105-6° | White solid | Example 1 |
| 17. | 313 | 197° | White solid | Example 3 |
| 18. | 261 | — | oil | Example 5 |
| 19. | 293 | 93-95° | White solid | Example 3 |
| 20. | 279 | 115-117° | White solid | Example 9 |
| 21. | 267 | 86.5-87° | White solid | Example 6 |
| 22. | 346 | <40° | White solid | Example 7 |
| 23. | 275 | <40° | White solid | Example 8 |
| 24. | 307 | 186-187° | White solid | Example 3 |
| 25. | 307 | 172-173° | White solid | Example 3 |

TABLE 4

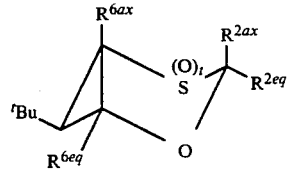

| Compound Number | $R^{2ax}$ | $R^{2eq}$ | $R^{6ax}$ | $R^{6eq}$ | Isomer Ratio | t |
|---|---|---|---|---|---|---|
| 22. | H | 4-(trimethylsilylethynyl) | H phenyl | Methyl | — | 0 |
| 23. | H | 4-ethynylphenyl | H | Methyl | 89 | 0 |
| | H | 4-ethynylphenyl | Methyl | H | 11 | |
| 24. | H | 4-ethynylphenyl | H | Methyl | — | 2 |
| 25. | 4-ethynylphenyl | H | H | Methyl | — | 2 |

Biological Activity

The following examples illustrate in a non-limiting manner the pesticidal activity of compounds of formula 1.

Spray Tests

The activity of the compounds of the invention was demonstrated by dissolving the compounds in acetone (5%) and then diluting in water: "Symperonic" (94.5%: 0.5%) to give an aqueous emulsion. This was used to treat the following insects.

*Musca domestica*

20 Female Musca were contained in a cardboard cylinder with gauze over either end. Solution of the compound was sprayed onto the insects so enclosed and mortality assessed after 48 hours at 25° C.

The following compounds were active at less than 1000 ppm:
7, 8, 15, 16, 19, 22

The following compounds were active at less than 200 ppm:
1, 3, 4, 5, 6, 9, 10, 12, 13, 14, 20, 21, 23, 24, 25.

*Plutella xyostella*

7 Plutella larvae were sprayed with solution of the compound and added to a chinese cabbage leaf which had been similarly sprayed and left to dry. Alternatively, 10 Plutella larvae were put onto leaf discs and sprayed with the solution of the compound. Mortality was assessed after 2 days at 25° C.

The following compounds were active at less than 1000 ppm: 3, 4, 5, 7, 8. 9, 17, 20
Active at 1000 ppm: 1, 13

The following compounds were active at less than 200 ppm: 2, 21

*Spodoptera littoralis*

Leaf discs of chinese cabbage were sprayed with solution of the compound and left to dry. They were then infested with 10 newly hatched first instar larvae. Mortality was assessed after 72 hours.

The following compounds were active at less than 1000 ppm:
9

*Myzus persicae*

10 Adults were placed on a leaf disc of chinese cabbage. 24 Hours later the disc was sprayed with the solution of compound. Mortality was assessed after 2 days at 25° C.

The following compounds were active at less than 1000 ppm:
3, 4, 5, 8, 19, 22. 23, 25, 20
Active at 1000—13

The following compounds were active at 200 ppm:
9, 10, 12, 14, 21

*Diabrotica undecimounctata*

Filter paper and food were sprayed with a solution of the compound. Subsequently, the filter paper was infested with 10 second instar larvae. Mortality was assessed after 48 hours.

The following compounds were active at less than 1000 ppm:
1, 5, 6, 7, 8, 9, 10, 14, 17, 19, 23, 25
Active at 1000—16

The following compounds were active at less than 200 ppm:
4, 12, 13, 20, 21, 24.

The following examples illustrate, in a non-limiting manner, preferred aspects of the invention.

Formulations

| | | |
|---|---|---|
| 1. | Emulsifiable Concentrate | |
| | Compound of formula (I) | 10.00 |
| | Ethylan KEO | 20.00 |
| | Xylene | 67.50 |
| | Butylated Hydroxyanisole | 2.50 |
| | | 100.00 |
| 2. | Wettable Powder | |
| | Compound of formula (I) | 25.00 |
| | Attapulgite | 69.50 |
| | Sodium isopropylbenzene sulphonate | 0.50 |
| | Sodium salt of condensed naphthalene sulphonic acid | 2.50 |
| | Butylated hydroxytoluene | 2.50 |
| | | 100.00 |
| 3. | Dust | |
| | Compound of formula (I) | 0.50 |
| | Butylated Hydroxyanisole | 0.10 |
| | Talc | 99.40 |
| | | 100.00 |
| 4. | Bait | |
| | Compound of formula (I) | 40.25 |
| | Icing Sugar | 59.65 |
| | Butylated hydroxy toluene | 0.10 |
| | | 100.00 |
| 5. | Lacquer | |
| | Compound of formula (I) | 0.10 |
| | Piperonyl Butoxide | 0.50 |
| | Butylated Hydroxyanisole | 10.10 |
| | High aromatic white spirit | 92.00 |
| | | 100.00 |
| 6. | Aerosol | |
| | Compound of formula (I) | 0.30 |
| | Butylated Hydroxy anisole | 0.10 |
| | 1,1,1-Trichloroethane | 4.00 |
| | Odourless Kerosene | 15.60 |
| | Arcton 11/12. 50:50 mix | 80.00 |
| | | 100.00 |
| 7. | Spray | |
| | Compound of formula (I) | 0.10 |
| | Butylated Hydroxyanisole | 0.10 |
| | Xylene | 10.00 |
| | Odourless Kerosene | 89.80 |
| | | 100.00 |
| 8. | Potentiated Spray | |
| | Compound of formula (I) | 0.10 |
| | Piperonyl Butoxide | 0.50 |
| | Butylated Hydroxyanisole | 0.10 |
| | Xylene | 10.10 |
| | Odourless Kerosene | 89.20 |
| | | 100.00 |

What is claimed is:
1. A compound of the formula (I):

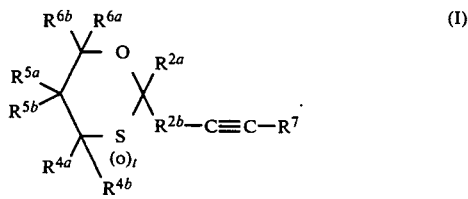

which contains between 10 and 27 carbon atoms, and wherein t is selected from 0, 1 and 2; $R^{2a}$ is hydrogen, methyl, or ethyl; $2^{2b}$ is a single bond, a $C_{5-7}$ cycloalkyl group or a group $(CH_2)_{n'}(X)_m(CH_2)_n$, optionally substituted by one to six halo atoms, which are the same or different, and/or by one or two alkyl groups optionally substituted by halo, where n is 0, 1 or 2, X is oxygen, sulphur or CH=CH, m is 0 or 1 and n' is 0 to 4, the sum or n, m and n' is between 0 and 6, or $R^{2b}$ is a para-substituted 6-membered aromatic ring additionally optionally substituted by one to four halo atoms and/or by one or two cyano groups and/or by one or two $C_{1-4}$ haloalkyl, haloalkoxy or haloalkylthio groups, $R^7$ is hydrogen, halo or a $C_{1-5}$ hydrocarbyl group, optionally substituted by a hydroxy, $C_{1-4}$ alkoxy or $C_{1-7}$ acyloxy group derived from carboxylic acid and/or by one to five halo atoms which are the same or different and/or by a group $-(O)_vS(O)_r(O)_wR^8$ where $R^8$ is ·wherein $R^8$ is a $C_{1-4}$ hydrocarbyl aliphatic group optionally substituted by halo, v is 0 or 1, r is 0, 1 or 2 and w is 0 or 1, the sum of v, r and w being between 0 and 3, or $R^7$ is a group $SiR^9R^{10}R^{11}$ where $R^9$, $R^{10}$, and $R^{11}$ are the same or different and are each $C_{1-4}$ aliphatic groups, provided that $R^9$, $R^{10}$ and $R^{11}$ do not contain more than 10 carbon atoms in total; $R^{4a}$, $R^{4b}$, $R^{6a}$ and $R^{6b}$ are the same or different and are chosen from hydrogen, methyl, trifluoromethyl or cyano. $R^{5b}$ is a group

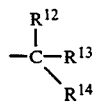

wherein $R^{12}$ is methyl, ethyl, chloro, bromo, methoxy, cyano, nitro, methoxymethyl, $C_{1-4}$ carbalkoxy or trifluoromethyl, $R^{13}$ is chloro, methyl or trifluoromethyl or

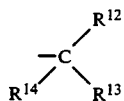

is a

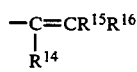

group wherein $R^{15}$ and $R^{16}$ are both hydrogen, methyl, trifluoromethyl, fluoro, chloro or bromo or $R^{15}$ is hydrogen and $R^{16}$ is fluoro, chloro or bromo, or

is a three or four membered ring, wherein $R^{12}$ is oxygen or a group $CR^{17}R^{18}$ wherein the groups $R^{17}$ and $R^{18}$ are the same or different and each is hydrogen, fluoro, chloro or bromo or methyl or ethyl optionally substituted by 1 to 5 fluoro atoms, when

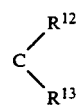

is a three membered ring $R^{13}$ is a group $CR^{17a}R^{18a}$ wherein $R^{17a}$, $R^{18a}$ are the same or different and each is hydrogen, fluoro, chloro or bromo or methyl or ethyl optionally substituted by 1 to 5 fluoro atoms, or when

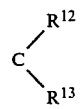

is a four membered ring $R^{13}$ is a group $CR^{17a}R^{18a}CR^{19}R^{20}$ wherein $R^{17a}$, $R^{18a}$ are as defined above, and $R^{19}$, and $R^{20}$ are the same or different and each is hydrogen, fluoro, chloro or bromo or methyl or ethyl optionally substituted by 1 to 5 fluoro atoms, and $R^{14}$ is hydrogen, methyl, trifluoromethyl, iodo, fluoro, chloro or bromo; and $R^{5b}$ is a hydrogen, methyl, hydroxy, methoxy, acetoxy, halo or trifluoromethyl.

2. The compound of claim 1 in which $R^{2b}$ contains between 0 and 8 carbon atoms and is single bond, a $C_{3-6}$ alkyl or alkenyl group or a phenyl or cyclohexyl group, each of which is optionally substituted by halo or $C_{1-3}$ haloalkyl.

3. The compound of claim 1 in which $R^{2b}$ is a phenyl group substituted at the 4-position by a group $C\equiv C-R^7$ and optionally substituted by one or two additional substituents at the 3- and/or 5-positions each selected from halo, $C_{1-4}$ haloalkyl, $C_{1-4}$ haloalkoxy, $C_{1-4}$ haloalkylthio or cyano and wherein the phenyl group is optionally substituted at the 2- and/or 6-positions by fluoro or chloro.

4. The compound of claim 1 in which $R^{2b}$ is phenyl substituted at the 4-position by a group $C\equiv C-R^{12}$ wherein $R^{12}$ is hydrogen, methyl, or ethyl each optionally substituted by hydroxy, methoxy, ethoxy, or acetoxy; or $R^{12}$ is a silyl group substituted by three $C_{1-4}$ alkyl groups, and wherein the phenyl group is additionally optionally substituted by fluoro or chloro.

5. The compound of claim 1 in which $R^{2b}$ is a single bond, a $C_{3-5}$ aliphatic chain optionally containing a double bond and/or an oxygen atom and/or a group $S(O)_q$ where q is 0, 1 or 2, optionally substituted by halo, $C_{1-4}$ alkyl or $C_{1-4}$ haloalkyl.

6. The compound of claim 1 in which $R^{2b}$ is a 1,4-disubstituted cyclohexyl group.

7. The compound of claim 1 in which $R^7$ is hydrogen, bromo, chloro, iodo or a $C_{1-5}$ aliphatic group derived from carboxylic acid optionally substituted by $C_{1-4}$ alkoxy, $C_{1-7}$ acyloxy, halo or hydroxy; or $R^7$ is $SiR^9R^{10}R^{11}$ wherein $R^9$, $R^{10}$ and $R^{11}$ are as defined above.

8. The compound of claim 1, in which $R^{2a}$ is hydrogen or methyl.

9. The compound of claim 1, in which $R^{4a}$, $R^{4b}$, $R^{6a}$ and $R^{6b}$ are all hydrogen.

10. The compound of claim 1, in which $R^{5a}$ is tertiary butyl or isopropyl.

11. The compound of claim 1, in which $R^{5b}$ is hydrogen or methyl.

12. A compound selected from the group consisting of:

5(e)-t-butyl-2(e)-4-ethynylphenyl)-1,3-oxathiane,
5(e)-t-butyl-2(e)-(ethynylphenyl)-1,3-oxathiane 3-oxide,
5(e)-t-butyl-2(e)-(4-ethynylphenyl)-1,3-oxathiane 3,3-dioxide,
5(e)-t-butyl-2(e)-(hex-5-ynyl)-1,3-oxathiane,
5(e)-t-butyl-2(e)-(hex-5-ynyl)-1,3-oxathiane 3,3-dioxide,
trans/cis-2-(hex-5-ynyl)-5-isopropyl-1,3oxathiane,
2(e)-(hex-5-ynyl)-5(e)-isopropyl-1,3-oxathiane 3,3-dioxide, trans/cis-2-(hex-5-ynyl)-5-isopropyl-1,3oxathiane 3,3-dioxide,
trans/cis-2-(4-ethynylcyclohexyl)-5-isopropyl-1,3-oxathiane,
2(e)-(4-ethynylphenyl)-5(e)-isopropyl-1,3-oxathiane 3,3-dioxide,
2(e)-(4-ethynylphenyl)-5(e)-isopropyl-1,3-oxathiane 3-oxide,
2(a)-(4-ethynylphenyl)-5(e)-isopropyl-1,3-oxathiane
2(e)-(4-ethynylphenyl)-5(e)-phenyl-1 3-oxathiane,
2(e)-(4-ethynylphenyl)-5(e)-phenyl-1,3-oxathiane 3,3-dioxide,
2(e)-(hex-5-ynyl)-5(e)-phenyl-1,3-oxathiane 3,3-dioxide,
5(e)-t-butyl-2(e)-(4-ethynyl-3-fluorophenyl)-1,3oxathiane,
trans/cis-5-t-butyl-2-(4-ethynylcyclohexyl)-1,3-oxathiane,
5(e)-t-butyl-6(e)-methyl-2(e)-(4-trimethylsilyl-ethynylphenyl)-1,3-oxathiane,
5(e)-t-butyl-2(e)-(4-ethynylphenyl)-6-methyl-1,3-oxathiane,
5(e)-t-butyl-2(e)-(4-ethynylphenyl)-6(e)-methyl-1,3-oxathiane 3,3-dioxide, or
5(e)-t-butyl-2(a)-(4-ethynylphenyl)-6(e)-methyl1,3-oxathiane 3,3-dioxide.

13. A pesticidal formulation comprising a pesticidally effective amount of a compound of claim 1, in admixture with one or more carriers or diluents.

14. A method for the control of arthropods which comprises administering to the arthropod or its environment an effective amount of a compound of claim 1.

15. A method for the control of helminths which comprises administering to the helminth or its environment an effective amount of a compound of claim 1.

16. A method for the control of arthropod and/or helminth infestations of plants and/or animals and/or stored products which comprises administering an effective amount of a compound of claim 1.

17. A compound of the formula:

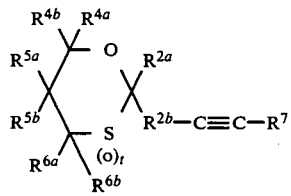

which contains between 10 and 27 carbon atoms, and wherein t is selected from 0, 1 and 2; $R^{2a}$ is hydrogen, methyl, or ethyl; $R^{2b}$ is a single bond, a $C_{5-7}$ cycloalkyl group or a group $(CH_2)_n(X)_m(CH_2)_{n'}$, optionally substituted by one to six halo atoms which are the same or different and/or by one or two alkyl groups optionally substituted by halo wherein n is 0, 1 or 2, X is oxygen, sulphur or CH=CH, m is 0 or 1 and n' is 0 to 4, the sum or n, m and n' is between 0 and 6, or $R^{2b}$ is a para-substituted 6-membered aromatic ring additionally optionally substituted by one to four halo atoms and/or by one or two cyano groups and/or by one or two $C_{1-4}$ haloalkyl, haloalkoxy or haloalkylthio groups, and $R^7$ is hydrogen, halo or a $C_{1-5}$ hydrocarbyl group, optionally substituted by a hydroxy, $C_{1-4}$ alkoxy or $C_{1-7}$ acyloxy group derived from carboxylic acid and/or by one to five halo atoms which are the same or different and/or by a group $-(O)_v S(O)_r(O)_w R^8$ wherein $R^8$ is a $C_{1-4}$ hydrocarbyl aliphatic group optionally substituted by halo, v is 0 or 1, r is 0, 1 or 2 and w is 0 or 1, the sum of v, r and w being between 0 and 3, or $R^7$ is a group $SiR^9 R^{10} R^{11}$ wherein $R^9$, $R^{10}$, and $R^{11}$ are the same or different and are each $C_{1-4}$ aliphatic groups provided that $R^9$, $R^{10}$ and $R^{11}$ do not contain more than 10 carbon atoms in total; $R^{4a}$, $R^{4b}$, $R^{6a}$ and $R^{6b}$ are the same or different and are chosen from hydrogen, methyl, trifluoromethyl or cyano, $R^{5b}$ is hydrogen, methyl, hydroxy, methoxy, acetoxy, halo or trifluoromethyl, and $R^{5a}$ is tert. butyl, cyclobutyl, 1-methyl-cyclopropyl or isopropyl.

18. The compound of claim 17, in which $R^{2b}$ is a single bond, a $C_{3-6}$ alkyl or alkenyl group, a phenyl or cyclohexyl group, each of which may be optionally substituted by halo or $C_{1-3}$ haloalkyl.

19. The compound of claim 17, in which $R^{2b}$ is a phenyl group, substituted at the 4-position by a group C≡C-$R^7$ and optionally substituted by one or two additional substituents at the 3-and/or 5-positions each selected from halo, $C_{1-4}$ haloalkyl, $C_{1-4}$ haloalkyl, $C_{1-4}$ haloalkoxy, $C_{1-4}$ haloalkylthio or cyano and wherein the phenyl group is optionally substituted at the 2-and/or 6-positions by fluoro or chloro.

20. The compound of claim 17, in which $R^{2b}$ is phenyl substituted at the 4-position by a group C≡C$R^{12}$ wherein $R^{12}$ is hydrogen, methyl, or ethyl each optionally substituted by hydroxy, methoxy, ethoxy, or acetoxy; or $R^{12}$ is a silyl group substituted by three $C_{1-4}$ alkyl groups, and wherein the phenyl group is additionally optionally substituted by fluoro or chloro.

21. The compound of claim 17, in which $R^{2b}$ is a single bond, a $C_{3-5}$ aliphatic chain optionally containing a double bond and/or an oxygen atom and/or a group $S(O)_q$ where q is 0, 1 or 2, optionally substituted by halo, $C_{1-4}$ alkyl or $C_{1-4}$ haloalkyl.

22. The compound of claim 17, in which $R^{2b}$ is a 1,4-disubstituted cyclohexyl group.

23. The compound of claim 17, in which $R^7$ is hydrogen, bromo, chloro, iodo or a $C_{1-5}$ aliphatic group derived from carboxylic acid optionally substituted by $C_{1-4}$ alkoxy, $C_{1-7}$ acyloxy, halo or hydroxy.

24. The compound of claim 17, in which $R^7$ is $SiR^9 R^{10} R^{11}$ wherein $R^9$, $R^{10}$ and $R^{11}$ are as defined in claim 17.

25. The compound of claim 17, in which $R^{5a}$ is tert butyl.

26. The compound selected from the group consisting of 5-t-Butyl-2-(4-ethynylphenyl)-1,3-oxathiane,
5(e)-t-Butyl-2(e)-(4-ethynylphenyl)-1,3-oxathiane 3-oxide, and
(e)-t-Butyl-2(e)-(4-ethynylphenyl)-1,3-oxathiane 3,3-dioxide.

27. A pesticidal formulation comprising a pesticidally effective amount of a compound of claim 17, in admixture with one or more carriers or diluents.

28. A method for the control of arthropods which comprises administering to the arthropod or its environment an effective amount of a compound of claim 17.

29. A method for the control of helminths which comprises administering to the helminth or its environment an effective amount of a compound of claim 17.

30. A method for the control of arthropod and/or helminth infestations of plants and/or animals and/or stored products which comprises administering an effective amount of a compound of claim 17.

* * * * *